United States Patent

Humbert et al.

[11] Patent Number: 4,588,731
[45] Date of Patent: May 13, 1986

[54] DERIVATIVES OF ISOXAZOLO[4,5-C]QUINOLINE(2H)-3-ONE AND METHOD OF PREPARATION AND USE AS ANXIOLYTIC AGENTS

[75] Inventors: Daniel Humbert, Fontenay-sous-Bois; Jean-Claude Gasc, Bondy; Peter F. Hunt, Gonesse, all of France

[73] Assignee: Roussel Uclaf, Paris, France

[21] Appl. No.: 747,665

[22] Filed: Jun. 21, 1985

[51] Int. Cl.$^4$ .................... A61K 31/42; C07D 498/02; C07D 215/00
[52] U.S. Cl. ..................................... 514/293; 546/83; 546/153
[58] Field of Search .................... 546/153, 83; 514/293

[56] References Cited

PUBLICATIONS

Fiese, L. F., Reagents for Organic Synthesis, 1967, pp. 478–479.

Primary Examiner—Henry R. Jiles
Assistant Examiner—J. Richter
Attorney, Agent, or Firm—Bierman, Peroff & Muserlian

[57] ABSTRACT

Novel isoxazoloquinolinones of the formula

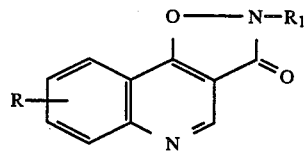

wherein R is selected from the group consisting of hydrogen, fluorine, chlorine, bromine, alkyl and alkoxy of 1 to 5 carbon atoms, —NO$_2$ and CF$_3$— and R$_1$ is phenyl optionally substituted by at least one member selected from the group consisting of halogen and alkyl and alkoxy of 1 to 5 carbon atoms having anxiolytic activity and their preparation and novel intermediates.

21 Claims, No Drawings

DERIVATIVES OF ISOXAZOLO[4,5-C]QUINOLINE(2H)-3-ONE AND METHOD OF PREPARATION AND USE AS ANXIOLYTIC AGENTS

OBJECTS OF THE INVENTION

It is an object of the invention to provide the novel compounds of formula I and their preparation and novel intermediates.

It is another object of the invention to provide novel anxiolytic compositions and a novel method of relieving anxiety in warm-blooded animals.

These and other objects and advantages of the invention will become obvious from the following detailed description.

THE INVENTION

The novel compounds of the invention are isoxazoloquinolinones of the formula

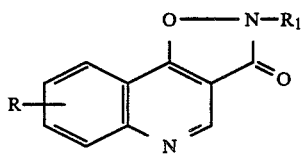

wherein R is selected from the group consisting of hydrogen, fluorine, chlorine, bromine, alkyl and alkoxy of 1 to 5 carbon atoms, —NO₂ and CF₃— and R₁ is phenyl optionally substituted by at least one member selected from the group consisting of halogen and alkyl and alkoxy of 1 to 5 carbon atoms.

Examples of alkyl and alkoxy of 1 to 5 carbon atoms are methyl, ethyl, n-propyl, isopropyl, isobutyl, methoxy, ethoxy, n-propoxy and isopropoxy. When R₁ is a substituted phenyl, the substitution may be at any position such as 2-, 3-, 4- or 3,4-, preferably at 4-position. The halogen may be fluorine or iodine, but preferably chlorine or bromine.

Among the preferred compounds of formula I are those wherein R is hydrogen or chlorine. Specific preferred compounds are 2-phenyl-isoxazolo(4,5-c)quinolin-3(2H)-one, 8-fluoro-2-phenyl isoxazolo(4,5-c)quinolin-3(2H)-one and 8-methoxy-2-phenyl isoxazolo (4,5-c)quinolo-3(2H)-one.

The novel process of the invention for the preparation of the compounds of formula I comprises reacting a compound of the formula

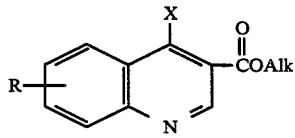

wherein Alk is alkyl of 1 to 3 carbon atoms, X is chlorine or bromine and R has the above definition with a hydroxylamine of the formula

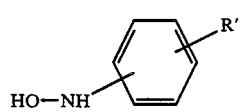

wherein R' has the above definition for the optional substituents of the phenyl.

Preferably, Alk is methyl, ethyl or propyl and most preferably ethyl and X is chlorine. The said reaction is preferably effected in an alkaline medium such as sodium hydride in tetrahydrofuran.

The compounds of formula II are known and the compounds of formula III are known or can be prepared by known processes such as Organique Synthese, Vol. 1, p. 445 or J.A.C.S., Vol. 78 (1956), p. 336.

Another process of the invention for the preparation of compounds of formula I comprises reacting a derivative of a compound of the formula

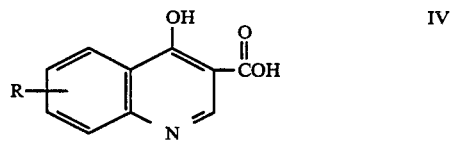

with a hydroxylamine of formula III to obtain a compound of the formula

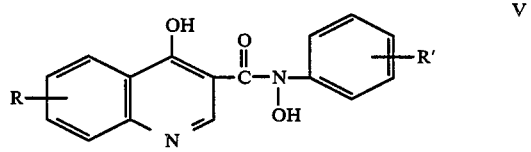

and cyclizing the latter to form the corresponding compound of formula I.

In a preferred mode of the process, the derivative of the compound of formula IV is the acid chloride which can be prepared by reacting the acid with thionyl chloride and the cyclization of the compounds of formula V is effected in the presence of triphenylphosphine and ethyl azodicarboxylate in the presence of a solvent such as dimethylformamide, methylene chloride or toluene.

The compounds of formula IV are known and may be prepared from the corresponding alkyl esters described in European patent application No. 67,772.

The novel anxiolytic compositions of the invention are comprised of an anxiolytically effective amount of at least one compound of formula I and an inert pharmaceutical carrier or excipient. The compositions may be in the form of tablets, dragees, capsules, granules, suppositories or injectable solutions or suspensions prepared in a known manner.

Examples of suitable excipients are talc, arabic gum, lactose, starch, magnesium stearate, cocoa butter, aqueous and non-aqueous vehicles, fatty substances of animal or vegetable origin, paraffinic derivatives, glycols, various wetting agents, dispersants and emulsifiers and preservatives.

Among the preferred compositions of the invention are those wherein R is hydrogen or chlorine. Specific preferred compounds are 2-phenyl-isoxazolo(4,5-c)quinolin-3-(2H)-one, 8-fluoro-2-phenyl isoxazolo(4,5-c)quinolin-3-(2H)-one and 8-methoxy-2-phenyl isoxazolo(4,5-c)quinolin-3-(2H)-one.

The compositions have a notable affinity for benzodiazepine receptors and are useful in the treatment of anxiety conditions such as chronic anxiety, possibly associated with insomnia or behavioural problems, anguish in adults and children and as a complement in neuroleptic or antidepressant treatment of psychotic or depressive conditions.

The novel method of the invention of relieving anxiety in warm-blooded animals, including humans, comprises administering to warm-blooded animals an anxiolytically effective amount of at least one compound of formula I. The compounds may be administered orally, rectally or parenterally and the usual daily dose is 0.015 to 7.15 mg/kg depending on the conditions treated, the method of administration and the specific compound. For example, the compound of Example 1 may be orally administered at 0.03 to 3 mg/kg for treatment of chronic aniexty.

In the following examples there are described several preferred embodiment to illustrate the invention. However, it should be understood that the invention is not intended to be limited to the specific embodiments.

EXAMPLE 1

2-phenylisoxazolo(4,5-c)quinolin-3-(2H)-one

A solution of 9 g of N-phenylhydroxylamine [described in Organique Synthese, Vol. 1, p. 445] was added dropwise at 0° C. with stirring under an inert atmosphere to a suspension of 3.85 g of 50% sodium hydride in 100 ml of tetrahydrofuran, and after stirring at 5° C. for 30 minutes, a solution of 18.8 g of ethyl 4-chloro-3-quinoline carboxylate in 100 ml of tetrahydrofuran was added at 0° C. The mixture was stirred for 16 hours at ambient temperature and after concentration to dryness under reduced pressure, the residue was taken up in ice. The mixture was extracted with methylene chloride and the organic phase was washed, dried, and concentrated to dryness. The residue was purified by chromatography on silica (eluent: ethyl acetate) to obtain 1.2 g of 2-phenylisoxazolo(4,5-c)quinolin-3-(2H)-one (corresponding to the 3rd eluted fraction) melting at 163° C. after crystallization from isopropyl ether.

| Analysis: | $C_{16}H_{10}N_2O_2$: molecular weight = 262.269 | | |
|---|---|---|---|
| Calculated: | % C 73.27 | % H 3.84 | % N 10.68 |
| Found: | 72.9 | 3.8 | 10.5 |

EXAMPLE 2

8-fluoro-2-phenylisoxazolo(4,5-c)quinolin-3-(2H)-one

STEP A: N,4-dihydroxy-6-fluoro-N-phenyl-3-quinoline carboxamide 6.2 g of 4-hydroxy-6-fluoro-3-quinoline carboxylic acid, 100 ml of anhydrous benzene and 14.28 g of thionyl chloride were refluxed with stirring for 16 hours and then the mixture was cooled. The acid chloride was separated, washed with benzene and dried under reduced pressure at ambient temperature. Small fractions of this product were added with stirring to a mixture cooled to 0° C. of 10 g of N-phenylhydroxylamine, 4.8 ml of pyridine and 50 ml of dichloromethane. The mixture was stirred at ambient temperature for 16 hours and the precipitate was separated, washed with water until chloride ions were eliminated to obtain 6.68 g of N,4-dihydroxy-6-fluoro-N-phenyl-3-quinoline carboxamide which after crystallization from dimethylformamide melted at 260° C.

STEP B: 8-fluoro-2-phenylisoxazolo(4,5-c)quinolin-3-(2H)-one

Into a mixture of 8.81 g of triphenylphosphine and 50 ml of dimethylformamide, 5.58 g of ethyl azodicarboxylate were poured at 10°-15° C. and after continued stirring for 15 minutes, 6.68 g of the product of Step A were added in small fractions. Stirring was maintained for 2 hours at 0° C. and for 16 hours at ambient temperature and the crystallized product was separated. The filtrate was poured into iced water, and extracted with dichloromethane. The organic phase was washed with water, dried and the solvent was eliminated. The residue was chromatographed on silica and eluted with a methylene chloride-ethyl acetate mixture (9-1) to obtain 0.92 g of 8-fluoro-2-phenylisoxazolo(4,5-c)quinolin-3-(2H)-one melting at 174° C.

EXAMPLE 3

7-methoxy-2-phenylisoxazolo(4,5-c)quinolin-3-(2H)-one

STEP A: N,4-dihydroxy-7-methoxy-N-phenyl-3-quinoline carboxamide

Using the procedure of Step A of Example 2, 5.48 g of 4-hydroxy-7-methoxy-3-quinoline carboxylic acid were reacted to obtain 4.05 g of N,4-dihydroxy-7-methoxy-N-phenyl-3-quinoline carboxamide melting at 260° C.

STEP B: 7-methoxy-2-phenylisoxazolo(4,5-c)quinolin-3-(2H)-one

Using the procedure of Step B of Example 2, 3.68 g of N,4-dihydroxy-7-methoxy-N-phenyl-3-quinoline carboxamide were reacted and after 18 hours at ambient temperature, the reaction mixture was poured into water and the products which crystallized were extracted with dichloromethane. The organic phase was washed with water and the solvent was eliminated. The residue was chromatographed on silica and eluted with a mixture of methylene chloride-ethyl acetate (9-1) to obtain 0.7 g of 7-methoxy-2-phenylisoxazolo(4,5-c)quinolin-3-(2H)-one melting at 170° C.

EXAMPLE 4

8-methoxy-2-phenylisoxazolo(4,5-c)quinolin-3-(2H)-one

STEP A: N,4-dihydroxy-6-methoxy-N-phenyl-3-quinolin carboxamide

Using the procedure of Step A of Example 2, 5.48 g of 4-hydroxy-6-methoxy-3-quinoline carboxylic acid were reacted to obtain 3.06 g of N,4-dihydroxy-6-methoxy-N-phenyl-3-quinolin carboxamide which after crystallization from acetic acid melted at 226° C.

STEP B: 8-methoxy-2-phenyl isoxazolo(4,5-c)quinolin-3-(2H)-one

Using the procedure of Step B of Example 2, 2.92 g of the product of Step A were reacted and after 18 hours of stirring, the insoluble matter was separated. The filtrate was poured into cooled water and the crystals formed were extracted with methylene chloride. The organic phase was washed with water, dried and the solvents eliminated. The residue was chromatographed on silica and eluted with a methylene chloride-ethyl acetate mixture (9-1) to obtain 0.9 g of 8-methoxy-2-phenyl isoxazolo(4,5-c)quinolin-3-(2H)-one melting at 140° C.

EXAMPLE 5

8-trifluoromethyl-2-phenylisoxazolo(4,5-c)quinolin-3-(2H)-one

STEP A: N,4-dihydroxy-N-phenyl-6-trifluoromethyl-3-quinoline carboxamide

Using the procedure of Step A of Example 2, 9 g of 4-hydroxy-6-trifluoromethyl-3-quinoline carboxylic acid were reacted to obtain 5.45 g of N,4-dihydroxy-N-phenyl-6-trifluoromethyl-3-quinoline carboxamide melting at 260° C. (decomposition).

STEP B: 8-trifluoromethyl-2-phenylisoxazolo(4,5-c)quinolin-3-(2H)-one

Using the procedure of Step B of Example 2, 5.43 g of the product of Step A were reacted to obtain 0.75 g of 8-trifluoromethyl-2-phenylisoxazolo(4,5-c)quinolin-3-(2H)-one melting at 175° C.

EXAMPLE 6

7-chloro-2-phenylisoxazolo(4,5-c)quinolin-3-(2H)-one

STEP A: 7-chloro-N,4-dihydroxy-N-phenyl-3-quinoline carboxamide

Using the procedure of Step A of Example 2, 9.6 g of 7-chloro-4-hydroxy-3-quinoline carboxylic acid were reacted and the suspension was concentrated. The residue was taken up in water and the precipitate was separated, washed with water until chloride ions were eliminated to obtain 10.87 g of 7-chloro-N,4-dihydroxy-N-phenyl-3-quinoline carboxamide which after crystallization from dimethylformamide melted at 260° C.

STEP B: 7-chloro-2-phenylisoxazolo(4,5-c)quinolin-3-(2H)-one

Using the procedure of Step B of Example 2, 9.95 g of the product of Step A were reacted and after stirring for 18 hours and separation, the filtrate was chromatographed on silica and eluted with a mixture of methylene chloride-ethyl acetate (9-1) to obtain 2.65 g of 7-chloro-2-phenylisoxazolo(4,5-c)quinolin-3-(2H)-one which was crystallized from isopropanol to obtain 1.7 g of the product melting at 172° C.

EXAMPLE 7

8-chloro-2-phenylisoxazolo(4,5-c)quinolin-3-(2H)-one

STEP A: 6-chloro-N,4-dihydroxy-N-phenyl-3-quinoline carboxamide

Using the procedure of Step A of Example 2, 9 g of 6-chloro-4-hydroxy-3-quinoline carboxylic acid were reacted to obtain 6.2 g of crude 6-chloro-N,4-dihydroxy-N-phenyl-3-quinoline car-boxamide.

STEP B: 8-chloro-2-phenylisoxazolo(4,5-c)quinolin-3-(2H)-one

Using the procedure of Step B of Example 2, 5.48 g of the product of Step A were reacted and after 18 hours of stirring, the solvent was concentrated under reduced pressure. The residue was diluted with 100 ml of dichloromethane and chromatographed on silica and eluted with a methylene chloride-ethyl acetate mixture (9-1) to obtain 3.46 g of impure product. The latter was crystallized from isopropanol to obtain 350 mg of 8-chloro-2-phenylisoxazolo(4,5-c)quinoline-3-(2H)-one melting at 174° C.

EXAMPLE 8

2-(4-chlorophenyl)-isoxazolo(4,5-c)quinolin-3-(2H)-one

STEP A: N,4-dihydroxy-N-(4-chlorophenyl)-3-quinoline carboxamide

Using the procedure of Step A of Example 6, 9.45g of 4-hydroxy-3-quinoline carboxamide and N-(4-chlorophenyl)-hydroxylamine acid were reacted to obtain 14.4 g of crude N,4-dihydroxy-N-(4-chlorophenyl)-3-quinoline carboxamide STEP B: 2-(4-chlorophenyl)isoxazolo(4,5-c)quinolin-3-(2H)-one Using the procedure of Step B of Example 2, 6.1 g of the product of Step A were reacted and after 18 hours of stirring any insoluble matter was filtered off. The filtrate was chromatographed on silica and eluted with a methylene chloride-ethyl acetate mixture (9-1) to obtain 4.8 g of 2-(4-chlorophenyl)isoxazolo(4,5-c) quinolin-3-(2H)-one which after crystallization from isopropanol melted at 156° C.

EXAMPLE 9

8-ethyl-2-phenylisoxazolo(4,5-c)quinolin-3-(2H)-one

STEP A: N,4-dihydroxy-6-ethyl-N-phenyl-3-quinoline carboxamide

Using the procedure of Step A of Example 6, 3.2 g of 6-ethyl-4-hydroxy-3-quinoline carboxylic acid were reacted and after washing the precipitate with water, it was crystallized from a dimethylformamide-water mixture (1-1) to obtain 3.48 g of N,4-dihydroxy-6-ethyl-N-phenyl-3-quinoline carboxamide melting at 218° C.

STEP B: 8-ethyl-2-phenylisoxazolo(4,5-c)quinolin-3-(2H)-one

Using the procedure of Step B of Example 2, 2.68 g of the product of Step A with cooling to −7° C. then letting the temperature rise to 20° C. and stirring for 24 hours were reacted. After separating and chromatographing the filtrate on silica and eluting with a methylene chloride-ethyl acetate mixture (9-1), 1.53 g of 8-ethyl-2-phenylisoxazolo(4,5-c)quinolin-3-(2H)-one were obtained which after crystallization from isopropanol melted at 136° C.

EXAMPLE 10

2-phenylisoxazolo(4,5-c)quinolin-3-(2H)-one

STEP A: N,4-dihydroxy-N-phenyl-3-quinoline carboxamide

Using the procedure of Step A of Example 2, 9.46 g of 4-hydroxy-3-quinoline carboxylic acid were reacted to obtain 10.4 g of N,4-dihydroxy-N-phenyl-3-quinoline carboxamide melting at ≃220° C. (decomposition).

STEP B: 2-phenyl isoxazolo(4,5-c)quinolin-3-(2H)-one

Using the procedure of Step B of Example 2, 5.6 g of the product of Step A were reacted and after extraction with methylene chloride of the products of the reacted medium, the residue was chromatographed on silica and eluted with an ethyl acetate-cyclohexane mixture (3-7). A second chromatography was carried out on silica with elution with a methylene chloride-ethyl acetate mixture (9-1) to obtain 1.1 g of 2-phenyl isoxazolo(4,5-c)quinolin-3-(2H)-one melting at 163° C.

EXAMPLE 11

Tablets were prepared of the formula: 10 mg of 2-phenylisoxazolo(4,5-c)quinolin-3-(2H)-one and sufficient excipient of lactose, starch, talc and magnesium stearate to obtain a final tablet weight of 100 mg.

PHARMACOLOGICAL STUDY

A. Affinity for benzodiazepine receptors

The technique was inspired by that of Mohler et al [Science, Vol. 198 p. 849–851 (1977] in which the cortex from the brains of male rats weighing on average 150 g were homogenized to a twentieth (weight/volume) in 0.32M sucrose. After centrifuging the homogenate at 1000 g for 10 minutes at 0° C., the supernatant was centrifuged at 30,000 g for 20 minutes at 4° C. The residue was suspended in 20 volumes of Tris buffer HCl 50 mM pH 7.4 and centrifuged at 30,000 g for 20 minutes at 4° C. The new residue obtained was placed in 50 ml of Krebs Tris buffer HCl pH 7.4

2 ml of the suspension in the presence of $^3$H diazepam at a concentration of $10^{-9}$M were then incubated for 30 minutes at 0° C: (i) alone, (ii) with increasing concentrations of the product to be tested or, (iii) to determine the non-specific fixation, with non-radioactive diazepam at a concentration of $10^{-6}$M. The incubated suspension were filtered on Whatman GF/C and the filters were washed twice with 5 ml of Krebs Tris buffer HCl pH 7.4 at 0° C. The radioactivity of the filters was measured by liquid scintillation and the activity of the product was expressed in C.I.50, the concentration inhibiting 50% of the specific bond of $^3$H diazepam. The results obtained are in Table I.

TABLE I

| Product of Example | C.I. 50 in nM |
|---|---|
| 1 | 120 |
| 2 | 400 |
| 4 | 2460 |

B. Acute toxicity

The lethal doses $LD_0$ of the different compounds tested after administration by oral route in mice were evaluated. The maximum dose not provoking any mortality in 8 days was called $LD_0$ and the results obtained are in Table II.

TABLE II

| Product of Example | $LD_0$ in mg/kg |
|---|---|
| 1 | ≧400 |
| 2 | ≧400 |
| 3 | ≧200 |
| 4 | 200 |
| 5 | ≧200 |
| 7 | ≧100 |

C. Activity on serous level of corticosterone after stress from noise.

Groups of 5 rats were formed the day before the test and placed in a quiet room. The compounds were administered orally the following day between 8 and 9 o'clock in the morning. One hour afterwards, stress was applied which consisted of taking the animals from the cage and placing them in a room where a radio was playing loudly (90 decibels), then half an hour later, giving them an intraperitoneal puncture without injection. Ten minutes after this, the rats were anesthetized with halothane and samples of blood were taken by decapitation. The levels of serous corticosterone were then determined.

The results are expressed in $DE_{50}$, that is to say in a dose of the compound tested which reduced the increase in the level of serous corticosterone by 50% in animals treated in comparison with the control animals. The results were $DE_{50}$ in mg/kg of <50 and <100 for the compounds of Examples 2 and 4, respectively. Stress was less noticeable in the treated animals and those animals had therefore a degree of anxiety less than that of the control animals.

Various modifications of the compounds and methods of the invention may be made without departing from the spirit or scope thereof and it is to be understood that the invention is intended to be limited only as defined in the appended claims.

What we claim is:

1. A isoxazoloquinolinones of the formula

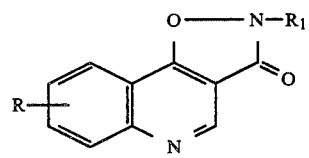

wherein R is selected from the group consisting of hydrogen, fluorine, chlorine, bromine, alkyl and alkoxy of 1 to 5 carbon atoms, $-NO_2$ and $CF_3-$ and $R_1$ is phenyl optionally substituted by at least one member selected from the group consisting of halogen and alkyl and alkoxy of 1 to 5 carbon atoms, 2. A compound of claim 1 wherein R is hydrogen 3. A compound of claim 1 wherein R is chlorine 4. A compound of claim 1 which is 2-phenyl isoxazolo (4,5-c)quinolin-3-(2H)-one.

5. A compound of claim 1 which is 8-fluoro-2-phenyl isoxazolo(4,5-c)quinolin-3-(2H)-one.

6. A compound of claim 1 which is 8-methoxy-2-phenyl isoxazolo(4,5-c)quinolin-3-(2H)-one.

7. A compound of the formula

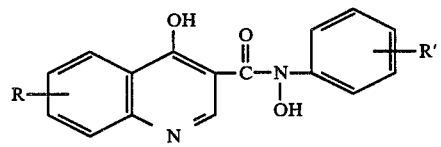

wherein R and R' have the definitions of claim 1.

8. An anxiolytic composition comprising an anxiolytically effective amount of at least one compound of claim 1 and an inert pharmaceutical carrier.

9. A composition of claim 8 wherein R is hydrogen.

10. A composition of claim 8 wherein R is chlorine.

11. A composition of claim 8 wherein the active compound is 2-phenyl isoxazolo(4,5-c)quinolin-3-(2H)-one.

12. A composition of claim 8 wherein the active compound is 8-fluoro-2-phenyl isoxazolo(4,5-c)quinolin-3-(2H)-one.

13. A composition of claim 8 wherein the active compound is 8-methoxy-2-phenyl isoxazolo(4,5-c)quinolin-3-(2H)-one.

14. A method of relieving anxiety in warm-blooded animals comprising administering to warm-blooded animals an anxiolytically effective amount of at least one compound of claim 1.

15. A method of claim 14 wherein R is hydrogen.

16. A method of claim 14 wherein R is chlorine.

17. A method of claim 14 wherein the active compound is 2-phenyl isoxazolo(4,5-c)quinolin-3-(2H)-one.

18. A method of claim 14 wherein the active compound is 8-fluoro-2-phenyl isoxazolo(4,5-c)quinolin-3-(2H)-one.

19. A method of claim 14 wherein the active compound is 8-fluoro-2-phenyl isoxaxolo(4,5-c)quinolin-3-(2H)-one.

20. A method for the preparation of a compound of claim 1 comprising reacting a compound of the formula

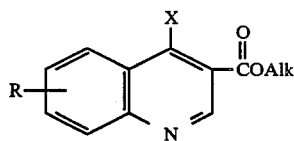

wherein Alk is alkyl of 1 to 3 carbon atoms, X is chlorine or bromine and R has the above definition with a hydroxylamine of the formula

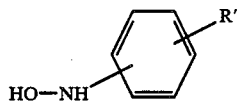

wherein R' has the above definition for the optional substituents of the phenyl.

21. A method for the preparation of a compound of claim 1 comprising reacting a derivative of a compound of the formula

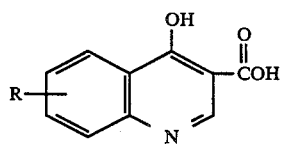

with a hydroxylamine of formula III to obtain a compound of the formula

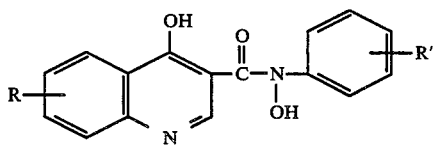

and cyclizing the latter to form the corresponding compound of claim 1.

* * * * *